(12) United States Patent
Terranova et al.

(10) Patent No.: US 7,659,421 B2
(45) Date of Patent: Feb. 9, 2010

(54) PHENYLBORONIC ACID COMPOUNDS AND INTERMEDIATES AND PROCESSES FOR THE PREPARATION THEREOF

(75) Inventors: Eric Terranova, Magagnosc (FR); Jean-Claude Pascal, Nice (FR)

(73) Assignee: Galderma Research & Development, Biot (FR)

( * ) Notice: Subject to any disclaimer, the term of this patent is extended or adjusted under 35 U.S.C. 154(b) by 93 days.

(21) Appl. No.: 11/454,859

(22) Filed: Jun. 19, 2006

(65) Prior Publication Data

US 2007/0015931 A1    Jan. 18, 2007

Related U.S. Application Data

(63) Continuation of application No. PCT/FR2004/003192, filed on Dec. 10, 2004.

(30) Foreign Application Priority Data

Dec. 18, 2003 (FR) ................... 03 14946

(51) Int. Cl.
  *C07F 5/04* (2006.01)
(52) U.S. Cl. ......................... 558/287; 562/7
(58) Field of Classification Search ................ 558/287; 562/7
  See application file for complete search history.

(56) References Cited

U.S. PATENT DOCUMENTS

2002/0143024 A1   10/2002   Murugesan et al.
2008/0019915 A1*  1/2008    Hadida-Ruah et al. ....... 424/9.2

FOREIGN PATENT DOCUMENTS

WO    WO 03/050067 A2    6/2003

OTHER PUBLICATIONS

Hadida-Ruah et al., 2008, CAS: 148:191855.*
Butler et al., 2006, CAS: 144:468206.*
International Search Report issued in PCT/FR2004/003192 dated Apr. 6, 2005.

* cited by examiner

*Primary Examiner*—Rei-tsang Shiao
(74) *Attorney, Agent, or Firm*—Buchanan, Ingersoll & Rooney P.C.

(57) ABSTRACT

Vitamin D derivatives, notably non-steroidal vitamin D derivatives, are prepared from novel disubstituted phenylboronic acid compounds having the formula (I):

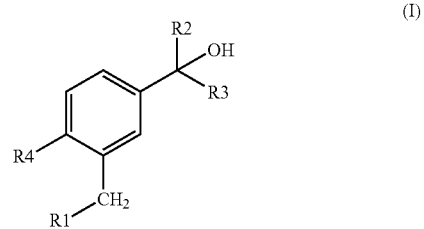

and also from the novel intermediates having the formulae (1), (2), (3) and (10):

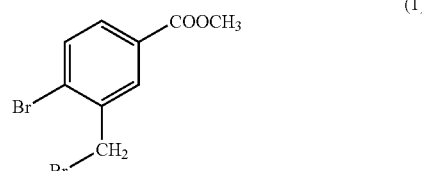

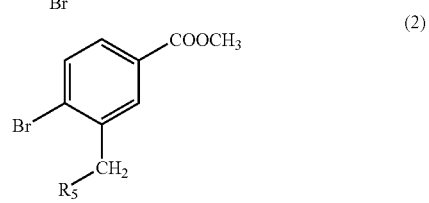

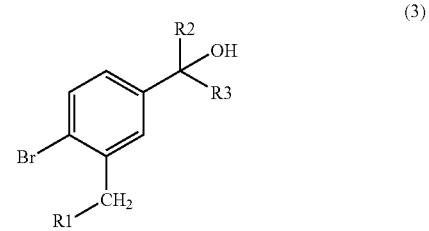

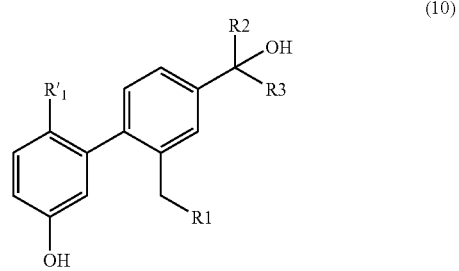

16 Claims, 4 Drawing Sheets

PHENYLBORONIC ACID COMPOUNDS AND INTERMEDIATES AND PROCESSES FOR THE PREPARATION THEREOF

CROSS-REFERENCE TO PRIORITY/PCT APPLICATIONS

This application claims priority under 35 U.S.C. § 119 of FR 03/14946, filed Dec. 18, 2003, and is a continuation of PCT/FR 2004/003192, filed Dec. 10, 2004 and designating the United States (published in the French language on Jul. 7, 2005 as WO 2005/061520 A1; the title and abstract were also published in English), each hereby expressly incorporated by reference and each assigned to the assignee hereof.

SUMMARY OF THE INVENTION

The present invention relates to novel disubstituted derivatives of phenylboronic acid, having the general formula (I):

in which:
R1 is a hydrogen atom or an alkyl radical having from 1 to 4 carbon atoms,
R2 and R3, which may be identical or different, are each an alkyl radical having from 1 to 4 carbon atoms,
R4 is the —B(OH)$_2$ radical or the radical of formula:

to processes for the preparation thereof and to their use as intermediates in the synthesis of non-steroidal vitamin D derivatives.

Phenylboronic acid derivatives can be employed in Suzuki-type coupling reactions and are important intermediates in the synthesis of non-steroidal vitamin D3 analogues. Such reactions have been described by the assignee hereof in WO 03/050067.

In WO 03/050067 the non-steroidal vitamin D derivatives of general formula (IVa) (see FIG. 1) are obtained from intermediate triflates of general formula (5) and boronic acid intermediates of general formula (6).

The preparation of the intermediate triflates of general formula (5) involves 3 synthesis steps and that of the boronic acid intermediates of general formula (6) involves 6 synthesis steps.

Figure 2:
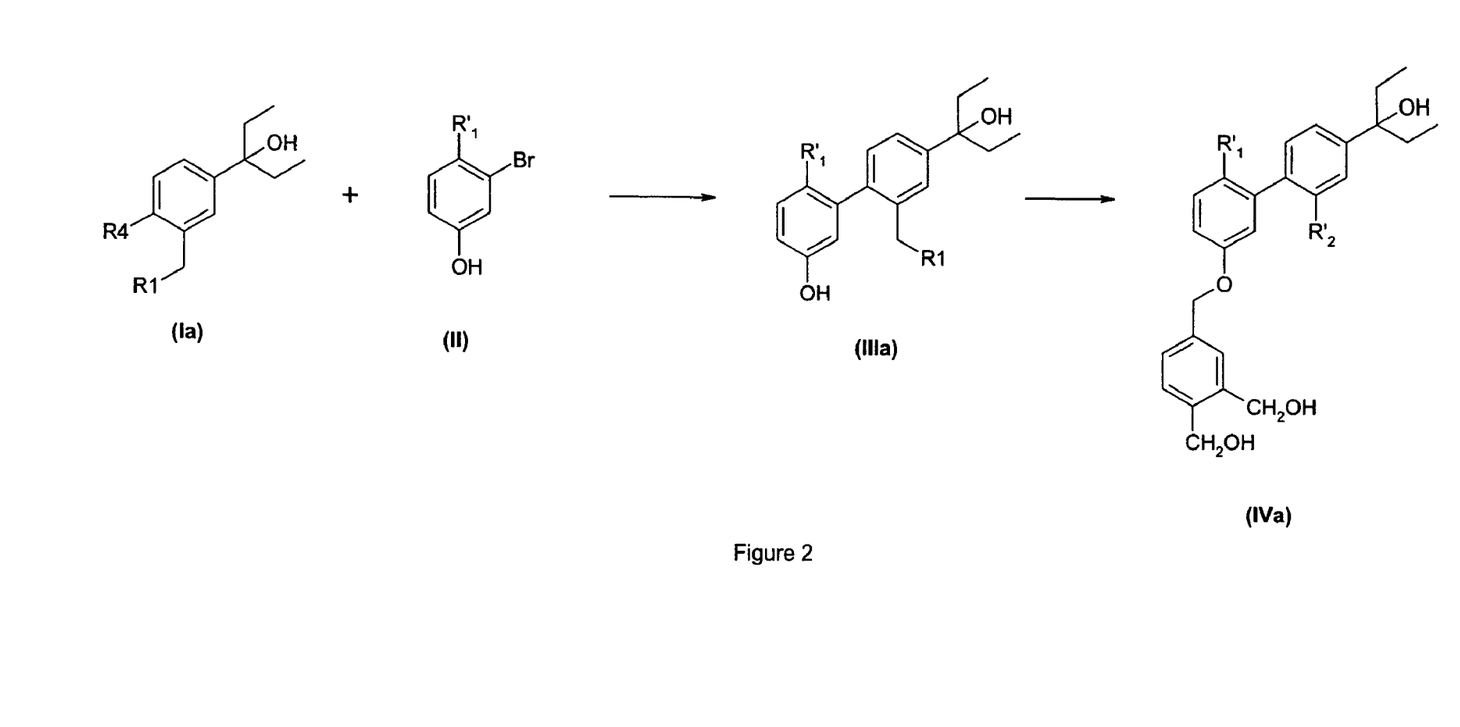

In the present invention the synthesis of the phenylboronic acids of general formula (Ia) takes place in 4 steps and involves the use of bromo derivatives of general formula (II) to obtain the non-steroidal vitamin D derivatives of general formula (IVa) according to FIG. 2. The bromo derivatives of general formula (II) are prepared in 3 steps.

Figure 1:
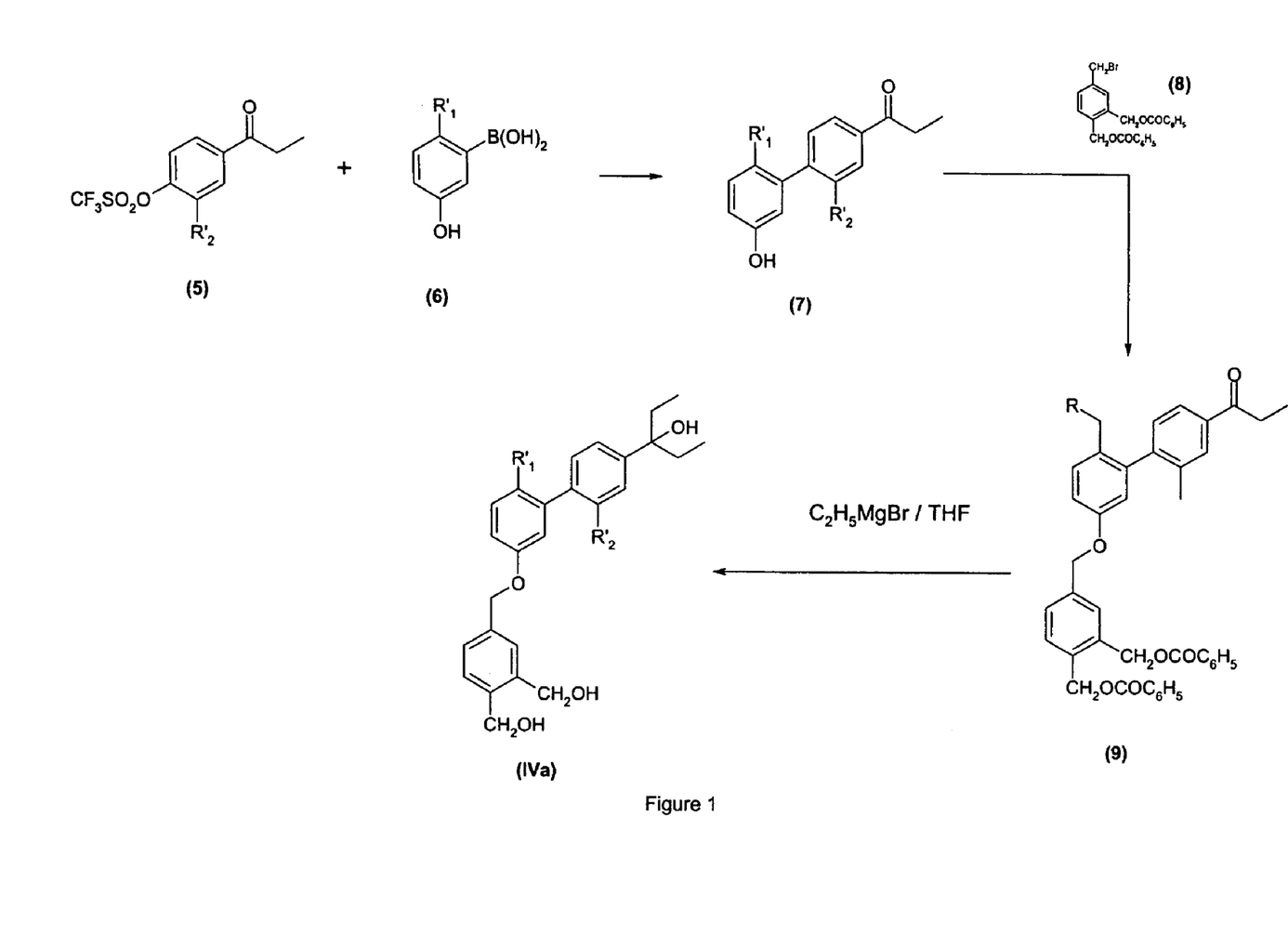
FIGS. 1-4 illustrate a variety of reaction schemes for the ultimate preparation of the compounds of formula (I).

The use of the phenylboronic acids of general formula (I) of the present invention therefore exhibits as its first advantage access to the biphenyl intermediates of general formula (III) in 7 steps in total (see FIG. 2), whereas the synthesis described previously, in WO 03/050067, involves 9 steps for access to the biphenyl intermediates of general formula (7) (FIG. 1).

The use of the phenylboronic acids of general formula (I) involves the utilization of bromo derivatives of general formula (II), which exhibits as a second advantage the avoidance of the protection and deprotection steps required in order to prepare the boronic acid intermediates of general formula (6) that are used in the preceding synthesis (FIG. 1). Moreover, the protection step was carried out with methoxymethyl chloride, a highly carcinogenic reactant which is prohibited on the industrial scale.

A third advantage provided by the use of the phenylboronic acids of general formula (I) is that they allow access to the biphenyl intermediates of general formula (III), in which the tertiary alcohol function is already present, whereas by proceeding via the biphenyl intermediates of general formula (7) as described in WO 03/050067 (FIG. 1) it is still necessary to convert the ketone function into a tertiary alcohol function.

A fourth advantage provided by the use of the phenylboronic acids of general formula (I) is that they allow access to the non-steroidal vitamin D derivatives of general formula (IVa) in fewer steps than with the synthesis as described in WO 03/050067 and with a better yield.

In the present invention novel phenylboronic acid derivatives have been synthesized via a novel process, which allows the above problems to be remedied.

The present invention thus features novel disubstituted derivatives of phenylboronic acid, having the general formula (I):

in which:
R1 is a hydrogen atom or an alkyl radical having from 1 to 4 carbon atoms,
R2 and R3, which may be identical or different, are each an alkyl radical having from of 1 to 4 carbon atoms, and
R4 is the —B(OH)$_2$ radical or the radical of formula:

DETAILED DESCRIPTION OF BEST MODE AND SPECIFIC/PREFERRED EMBODIMENTS OF THE INVENTION

According to the present invention an alkyl radical having 1 to 4 carbon atoms is a saturated or unsaturated, linear or cyclic, optionally branched radical which contains 1 to 4 carbon atoms and can be interrupted by a heteroatom, and preferably the alkyl radicals having 1 to 4 carbon atoms are methyl, ethyl, propyl, isopropyl, cyclopropyl, butyl, isobutyl or tert-butyl radicals.

The present invention also features the following novel intermediate compounds:

Where, for compounds (2) and (3), R1 is a hydrogen atom or an alkyl radical having from 1 to 4 carbon atoms, R2 and R3, which may be identical or different, are each an alkyl radical having from 1 to 4 carbon atoms and $R_5$ is an alkyl radical having from 1 to 4 carbon atoms.

The present invention likewise features employing the compounds (1), (2) and (3) for preparing non-steroidal vitamin D analogues and, in particular, as synthesis intermediates for preparing compounds of formula (I) according to the invention.

This invention, therefore, also features a process for synthesizing the subject novel phenylboronic acid derivatives of formula (I).

Figure 3:
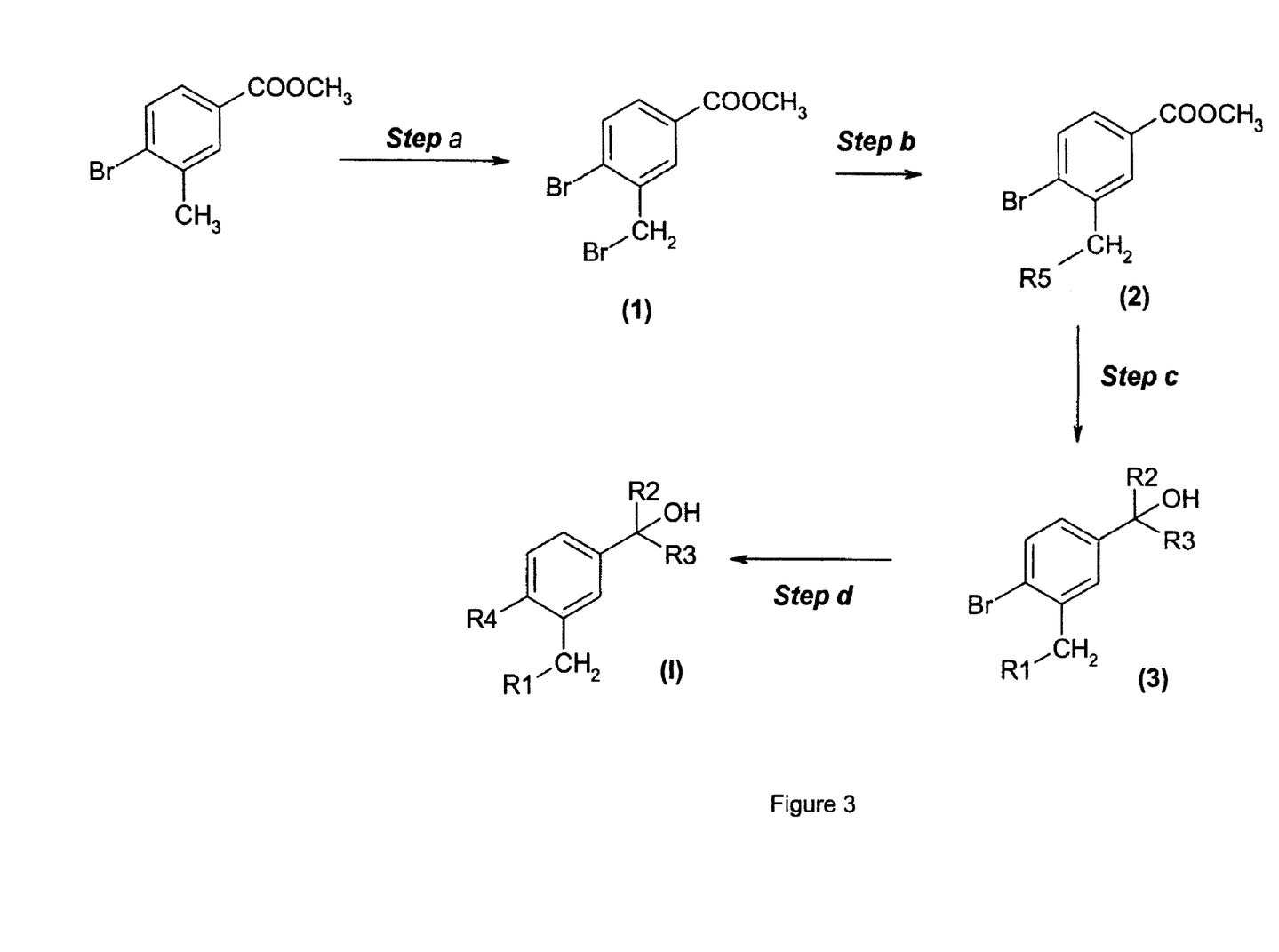

The synthesis of these novel phenylboronic acid compounds of general formula (I) in which R4 is the $B(OH)_2$ radical is carried out in 4 steps starting from methyl 4-bromo-3-methylbenzoate (commercial product) according to the scheme of FIG. 3.

Therefore, the process for preparing compounds of general formula (I) in which R4 is the $B(OH)_2$ radical comprises the following steps, steps a) and b) not being implemented in the specific case in which R1 is a hydrogen atom:

a) bromination in the benzylic position in the presence of a solvent, to give the compound (1):

b) substitution of the bromine introduced in step a) in the benzylic position by an alkyl chain $R_5$ containing 1 to 4 carbon atoms, to give the compound (2) as defined above:

c) conversion of the ester function of the intermediates of general formula (2) or of methyl 4-bromo-3-methylbenzoate into a tertiary alcohol function, using at least two equivalents of an organomagnesium compound of formula R2-MgX wherein X is a chlorine or bromine atom and R2 is a methyl, ethyl, propyl or butyl radical, to give the compound of general formula (3) as defined above:

d) conversion of the aromatic bromide of the intermediates of general formula (3) into phenylboronic acid of formula (I) in the presence of a solvent, a base and a trialkyl borate.

In greater detail, the steps of this process may be carried out as follows:

a. The first step entails performing a bromination in the benzylic position to give the intermediate (1). This halogenation reaction is described in the literature. Various brominating agents may be used, such as, for example, bromine (K. Smith et al., *J. Chem. Soc. Perkin. Trans., I*, 2000, 2745), N-bromosuccinimide (P. Liu et al., *Synthesis*, 2001, 2078), sodium bromate (D. Kikuchi et al., *J. Org. Chem.*, 1998, 6023) or else 1,3-dibromo-5,5-dimethylhydantoin (H. Jendralla et al., *Liebigs Ann. Chem.*, 1995, 1253). This reaction is carried out most often in chlorinated solvents or in ethers. The brominating agent used with preference is N-bromosuccinimide at dichloromethane reflux. Preferably, benzoyl peroxide is also used, in a catalytic amount, as a free-radical reaction initiator. In order to activate the free-radical reaction the reaction mixture is irradiated with a 1000 watt lamp.

This step provides the intermediate (1):

b. The second step entails substituting the bromine introduced in step 1 in the benzylic position by an alkyl chain R'1 containing 1 to 4 carbon atoms. In order to promote this substitution reaction the nucleophilic character of the alkyl group R'1 is increased by using an organometallic reagent R'1-M in which M is a metal atom such as magnesium, copper or else zinc. This reaction is described in the literature (B. H. Lipshutz and S. Sengupta, *Organic Reactions*, 1992, 41, 135). Preferably, copper in the form of copper iodide is employed in the presence of an organomagnesium compound R'1-MgX (X=Br, Cl, I) in order to generate an organocuprate. This reaction may be carried out in ethereal solvents. Preferably the ethereal solvent used is tetrahydrofuran. The reaction is carried out at low temperature, preferably from −40° C. and 0° C., more particularly from −40° C. and −20° C.

This step provides the intermediates of general formula (2), the radicals of which are defined above.

c. The third step entails converting the ester function of the intermediates of general formula (2) or of methyl 4-bromo-3-methylbenzoate into a tertiary alcohol function, using at least two equivalents of an organomagnesium compound of formula R2-MgX, wherein X is a chlorine, bromine or iodine atom and R2 is an alkyl radical having 1 to 4 carbon atoms. This reaction is widely described in the literature. This reaction may be carried out in ethereal solvents. Preferably, the ethereal solvent used is tetrahydrofuran. The reaction is preferably carried out at a temperature of from −20° C. and +20° C., more particularly from −10° C. and +10° C.

This step provides the intermediates of general formula (3), the radicals of which are defined above.

d. The fourth step entails converting the aromatic bromide of the intermediates of general formula (3) into phenylboronic acid of formula (I). This reaction, which is well documented in the literature (N. Miyaura & A. Suzuki, *Chem. Rev.*, 1995, 95, 2457), is carried out in tetrahydrofuran at temperatures of from −78° C. and −20° C., preferably from −78° C. and −40° C. From 2 and 4 equivalents of a strong base are used such as butyllithium, preferably from 2.5 and 3.5 equivalents, and a trialkyl borate is used, such as trimethyl borate or triisopropyl borate. From 2 and 4 equivalents of the latter are used, preferably from 2.5 and 3.5 equivalents.

According to another embodiment according to the invention, the synthesis of these novel phenylboronic acid derivatives of general formula (I) in which R4 is the radical of formula:

is carried out in 4 steps starting from methyl 4-bromo-3-methylbenzoate (commercial product) according to the scheme of FIG. 3.

The first three steps are similar to the process described above.

Therefore, the process for preparing compounds of general formula (I) in which R4 is the radical comprises the following steps, steps a) and b) not being implemented in the specific case in which R1 is a hydrogen atom:

a) bromination in the benzylic position in the presence of a solvent, to give the compound (1):

b) substitution of the bromine introduced in step a) in the benzylic position by an alkyl chain R5 containing 1 to 4 carbon atoms, to give the compound (2) as defined above:

c) conversion of the ester function of the intermediates of general formula (2) or of methyl 4-bromo-3-methylbenzoate into a tertiary alcohol function, using at least two equivalents of an organomagnesium compound of formula R2-MgX wherein X is a chlorine or bromine atom
and R2 is a methyl, ethyl, propyl, butyl or isobutyl radical to give the compound of general formula (3) as defined above:

(3)

d) conversion of the aromatic bromide into aryl boronate in the presence of a solvent, a catalyst, a base and pinacolborane or pinacoldiborane, to give the compound of general formula (I).

In greater detail, the steps of this process may be carried out as follows:

a. The first step entails performing a bromination in the benzylic position to give the intermediate (1). This halogenation reaction is described in the literature. Various brominating agents may be used, such as, for example, bromine (K. Smith et al., *J. Chem. Soc. Perkin. Trans.*, I, 2000, 2745), N-bromosuccinimide (P. Liu et al., *Synthesis,* 2001, 2078), sodium bromate (D. Kikuchi et al., *J. Org. Chem.,* 1998, 6023) or else 1,3-dibromo-5,5-dimethylhydantoin (H. Jendralla et al., *Liebigs Ann. Chem.,* 1995, 1253). This reaction is carried out most often in chlorinated solvents or in ethers. The brominating agent used with preference is N-bromosuccinimide at dichloromethane reflux. Preferably, benzoyl peroxide is also used, in a catalytic amount, as a free-radical reaction initiator. In order to activate the free-radical reaction the reaction mixture is irradiated with a 1000 watt lamp.

This step provides the intermediate (1):

(1)

b. The second step entails substituting the bromine introduced in step 1 in the benzylic position by an alkyl chain R'1 containing 1 to 4 carbon atoms. In order to promote this substitution reaction the nucleophilic character of the alkyl group R'1 is increased by using an organometallic reagent R'1-M in which M is a metal atom such as magnesium, copper or else zinc. This reaction is documented in the literature (B. H. Lipshutz and S. Sengupta, *Organic Reactions,* 1992, 41, 135). Preferably, copper in the form of copper iodide is employed in the presence of an organomagnesium compound R'1-MgX (X=Br, Cl, I) in order to generate an organocuprate. This reaction may be carried out in ethereal solvents. Preferably the ethereal solvent used is tetrahydrofuran. The reaction is carried out at low temperature, preferably from −40° C. and 0° C., more particularly from 40° C. and −20° C.

This step provides the intermediates of general formula (2), the radicals of which are defined above.

(2)

c. The third step entails converting the ester function of the intermediates of general formula (2) or of methyl 4-bromo-3-methylbenzoate into a tertiary alcohol function, using at least two equivalents of an organomagnesium compound of formula R2-MgX, wherein X is a chlorine, bromine or iodine atom and R2 is an alkyl radical having 1 to 4 carbon atoms. This reaction is widely described in the literature. This reaction may be carried out in ethereal solvents. Preferably, the ethereal solvent used is tetrahydrofuran. The reaction is preferably carried out at a temperature of from −20° C. and +20° C., more particularly from −10° C. and +10° C.

This step provides the intermediates of general formula (3), the radicals of which are defined above.

(3)

d. In this fourth step, the aromatic bromide of the intermediates of general formula (3) may be converted into aryl boronate. This reaction, which is also well described in the literature (a/ M. Murata et al., *J. Org. Chem.,* 1997, 62, 6458; b/ T. Ishiyama et al., *J. Org. Chem.,* 1995, 60, 7508), is carried out in solvents such as DMF, tetrahydrofuran, DMSO or else dioxane. The reaction temperatures used are generally close to the reflux temperatures of the solvents. Generally, use is made of a palladium catalyst, preferably dichloro[1,1'-ferrocenylbis(diphenylphosphane)]palladium(II) dichloromethane or Pd(dppf)Cl$_2$, a base, preferably potassium acetate or triethylamine, preferably from 2.5 and 3.5 equivalents, and a boron tetraalkoxide, preferably pinacolborane or pinacoldiborane. From 1 and 1.5 equivalents of the latter are used, preferably from 1.0 and 1.2 equivalents.

The present invention likewise features the use of the disubstituted derivatives of phenylboronic acid of formula (I) and the compounds (1), (2) and (3) as synthesis intermediates for preparing vitamin D derivatives.

Preferably, the compounds (I), (1), (2) and (3) according to the invention are used as intermediates in the synthesis of non-steroidal vitamin D derivatives displaying vitamin D activity.

More preferably, the non-steroidal vitamin D derivatives are compounds of formula (IV):

(IV)

in which:
- R1 is a hydrogen atom or an alkyl radical having from 1 to 4 carbon atoms,
- R2 and R3, which may be identical or different, are each an alkyl radical having from 1 to 4 carbon atoms, and
- R'$_1$ is an alkyl radical having from 1 to 4 carbon atoms.

Figure 4:
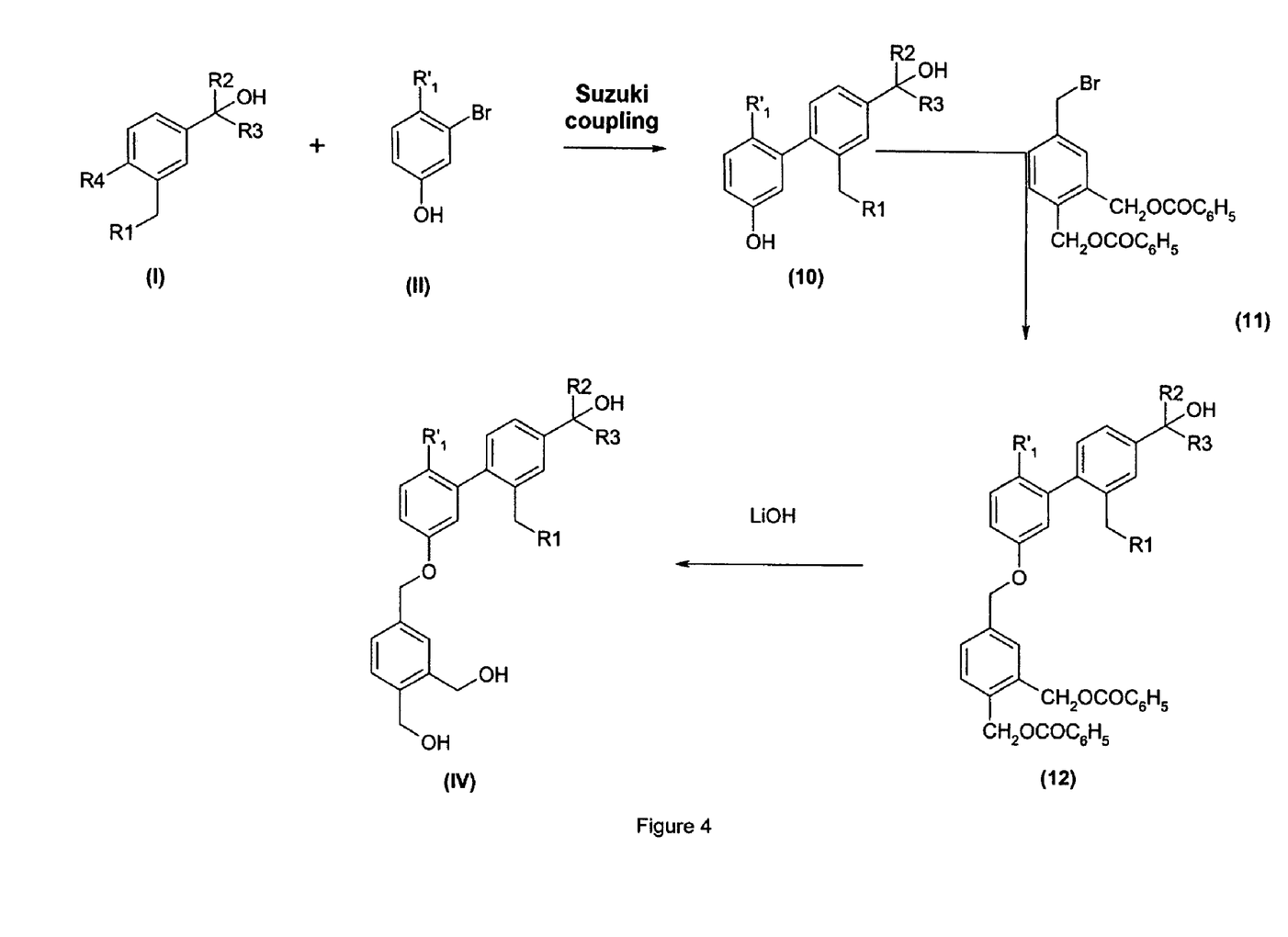

In the preferred embodiment according to the invention, the compounds according to the invention are therefore employed in the synthesis according to the scheme indicated in FIG. 4.

According to the invention, the compounds of formula (IV) are preferably prepared from the compound (12) obtained according to the reaction scheme of FIG. 4. Compound (12) may be obtained from phenylboronic acid derivative compounds of general formula (I) according to the invention. A first reaction is a Suzuki coupling reaction from the derivatives of general formula (I) according to the invention and an aryl bromide of general formula (II). The Suzuki reaction product, of general formula (10), is fused with the benzyl bromide (11) in the presence of a base such as, for example, potassium carbonate, to give the compounds of general formula (12). Subsequently, a reaction is employed in accordance with methods which are well known to one skilled in the art—for example, and without limitation, such as described in WO 03/050067, which allow the compound (IV) to be obtained from the compound (12).

The present invention therefore features the process for preparing compounds of formula (IV) from phenylboronic acids of the present invention according to the following steps:

a) A Suzuki coupling reaction from the compounds of general formula (I)

in which:
- R1 is a hydrogen atom or an alkyl radical having from 1 to 4 carbon atoms,
- R2 and R3, which may be identical or different, are each an alkyl radical having from 1 to 4 carbon atoms, and R4 is the —B(OH)$_2$ radical or the radical of formula:

and an aryl bromide of general formula (II):

(II)

in which:
- R'$_1$ is an alkyl radical having from 1 to 4 carbon atoms, to give the compound of general formula (10):

(10)

in which:
- R1 is a hydrogen atom or an alkyl radical having from 1 to 4 carbon atoms,
- R2 and R3, which may be identical or different, are each an alkyl radical having from 1 to 4 carbon atoms, and
- R'$_1$ is an alkyl radical having from 1 to 4 carbon atoms;

b) the Suzuki reaction product, of general formula (10), is fused with the benzyl bromide (11) in the presence of a base, such as potassium carbonate:

(11)

c) liberation of the alcohol functions of the compound (11) to give the compound (IV).

The present invention likewise features the compounds of formula (10), intermediates in the process defined above, of the following formula:

in which:
- R1 is a hydrogen atom or an alkyl radical having from 1 to 4 carbon atoms,
- R2 and R3, which may be identical or different, are each an alkyl radical having from 1 to 4 carbon atoms, and
- R'$_1$ is an alkyl radical having from 1 to 4 carbon atoms; and their use in the synthesis of vitamin D analogues as described above and in FIG. 2.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Step 1: Preparation of Methyl 4-bromo-3-bromomethylbenzoate

In a 6-liter reactor equipped with a condenser, a central mechanical stirrer and a thermometer, introduce 575 g (2.5 mol) of methyl 4-bromo-3-methylbenzoate, 3 liters of methylene chloride, 494 g (2.75 mol) of N-bromosuccinimide and 17 g of benzoyl peroxide (0.05 mol; 70% in water). Heat the mixture at reflux under irradiation with a 1000 watt lamp for 10 h. Wash the mixture twice with 1 liter of water, then with 1 liter of saturated sodium chloride solution. Evaporate the methylene chloride. Recrystallize the crude product obtained from heptane. This gives 596 g of methyl 4-bromo-3-bromomethylbenzoate in the form of off-white crystals (Yield=77%)

Melting point: 100-101° C.

$^1$H NMR (CDCl$_3$; 400 MHz): 3.94 (s; 3H); 4.64 (s; 2H); 7.68 (d; 1H; Jo=8.3 Hz); 7.83 (dxd; 1H; Jo=8.3 Hz and Jm=2.0 Hz); 8.14 (d; 1H; Jm=2.0 Hz)

Step 2: Preparation of Methyl 4-bromo-3-propylbenzoate

In a 6-liter reactor equipped with a condenser, a central mechanical stirrer, a thermometer and a dropping funnel, introduce under nitrogen 141 g (0.46 mol) of methyl 4-bromo-3-bromomethylbenzoate, 4 liters of tetrahydrofuran and 8.9 g (0.045 mol) of copper (I) iodide. Cool the mixture to −40° C. using a bath of acetonitrile and dry ice. Add 168 cm$^3$ of a 3M solution of ethylmagnesium bromide in diethyl ether and then allow the reaction temperature to increase to 0° C. After two hours of reaction hydrolyze the reaction mixture with 1 liter of 2.5M ammonium chloride solution. Separate the phases and extract the aqueous phase with 0.7 liter of methylene chloride. Combine the organic phases and evaporate the solvents. Pour heptane onto the product obtained and filter off the insoluble product which has formed. Evaporate the heptane and purify the resulting product by chromatography on silica gel (heptane/ethyl acetate=95/5). This gives 51 g of methyl 4-bromo-3-propylbenzoate in the form of colorless oil.
(Yield=43%)

$^1$H NMR (CDCl$_3$; 400 MHz): 1.01 (t; 3H; J$_1$=7.3 Hz); 1.68 (broad unresolved peak; 2H); 2.76 (t; 2H; J$_2$=7.6 Hz); 3.92 (s; 3H); 7.61 (d; 1H; Jo=8.3 Hz); 7.71 (dxd; 1H; Jo=8.3 Hz and Jm=1.8 Hz); 7.89 (d; 1H; Jm=1.8 Hz)

Step 3: Preparation of 3-(4-Bromo-3-propylphenyl)pentan-3-ol

In a 1-liter three-necked round-bottomed flask, equipped with a magnetic stirrer, a thermometer and a dropping funnel, introduce under nitrogen 47 g (0.18 mol) of methyl 4-bromo-3-propylbenzoate in solution in 250 ml of tetrahydrofuran. Cool the mixture to −5° C. with the aid of a bath of ice and sodium chloride. Add 134 cm$^3$ of a 3M solution of ethylmagnesium bromide in diethyl ether, then allow the reaction temperature to increase without exceeding 5° C. After three hours of reaction, hydrolyze the reaction mixture with 170 cm$^3$ of 2.5M ammonium chloride solution. Extend the organic phase with 200 cm$^3$ of ethyl acetate. Separate the phases and extract the aqueous phase with 2×200 cm$^3$ of methylene chloride. Combine the organic phases, dry them over sodium sulfate and evaporate the solvents. This gives 49.8 g of 3-(4-bromo-3-propylphenyl)pentan-3-ol in the form of colorless oil.
(Yield=96%)

¹H NMR (CDCl₃; 400 MHz): 0.77 (t; 6H; J₂=7.4 Hz); 1.00 (t; 3H; J₁=7.3 Hz); 1.68 (broad unresolved peak; 2H); 1.83 (broad unresolved peak; 4H); 2.73 (t; 2H; J₂=7.7 Hz); 7.05 (dxd; 1H; Jo=8.3 Hz and Jm=2.2 Hz); 7.24 (d; 1H; Jm=2.2 Hz); 7.48 (d; 1H; Jo=8.3 Hz)

Step 4: Synthesis of 4-(1-Ethyl-1-hydroxypropyl)-2-propylphenylboronic acid In a three-necked flask, introduce under nitrogen 5 g of 3-(4-bromo-3-propylphenyl)pentan-3-ol (17.5 mmol) and 50 cm³ of tetrahydrofuran. Cool the mixture to −70° C. and add dropwise 17.5 cm³ (43.7 mmol) of a 2.5M solution of n-butyllithium in hexane, over 30 minutes. Leave the reaction mixture for approximately 2 h with stirring at −70° C. and then add dropwise 10 cm³ of triisopropylborate (43.7 mmol), over 20 minutes. Leave the reaction mixture with stirring for 4 h, allowing the temperature to increase to −40° C. Hydrolyse the mixture with saturated NH₄Cl solution and extract twice with ethyl acetate. Wash the combined organic phases with saturated sodium chloride solution and evaporate the solvents under vacuum. This gives 5.4 g of a colorless oil, which is chromatographed on silica gel (heptane/ethyl acetate=3/1). This gives 1.92 g of 4-(1-ethyl-1-hydroxypropyl)-2-propylphenylboronic acid in the form of a highly viscous oil. (Yield=44%)

Example 2

Step 1: Preparation of 3-(4-Bromo-3-methylphenyl)pentan-3-ol

In a 4-liter SVL reactor equipped with a magnetic stirrer, a thermometer and a dropping funnel, introduce under nitrogen 198.7 g (0.867 mol) of methyl 4-bromo-3-methylbenzoate in solution in 1 liter of tetrahydrofuran. Cool the mixture to −5° C. with the aid of a bath of ice and sodium chloride. Add 636 cm³ of a 3M solution of ethylmagnesium bromide in diethyl ether, then allow the reaction temperature to increase to ambient temperature. After four hours of reaction, hydrolyze the reaction mixture with 2 liters of a 1 N hydrochloric acid solution. After decanting and separation, extract the aqueous phase with 0.5 liter of ethyl acetate. Wash the combined organic phases with 0.4 liter of water (3×). After drying over sodium sulfate, the product obtained after evaporation of the solvents is purified by chromatography on silica gel (heptane/ethyl acetate=95/5). This gives 150.2 g of 3-(4-bromo-3-methylphenyl)pentan-3-ol in the form of a colorless oil (Yield=67%)

¹H NMR (CDCl₃; 400 MHz): 0.79 (t; 6H; J₂=7.4 Hz); 1.63 (s; 1H); 1.83 (broad unresolved peak; 4H); 2.42 (s; 3H); 7.05 (dxd; 1H; Jo=8.3 Hz and Jm=2.2 Hz); 7.27 (d; 1H; Jm=2.2 Hz); 7.48 (d; 1H; Jo=8.3 Hz)

Step 2: Synthesis of 4-(1-Ethyl-1-hydroxypropyl)-2-methylphenylboronic acid

In a three-necked flask, introduce under nitrogen 5 g of 3-(4-bromo-3-methylphenyl)pentan-3-ol (19.4 mmol) and 50 cm³ of tetrahydrofuran. Cool the mixture to −70° C. and add dropwise 23.3 cm³ (58 mmol) of a 2.5M solution of n-butyllithium in hexane, over 30 minutes. Leave the mixture for approximately 2 h with stirring at −70° C. and then add dropwise 13.5 cm³ of triisopropyl borate (58 mmol), over 20 minutes. Leave the mixture with stirring for 3 h, allowing the temperature to increase to −10° C. Hydrolyse the mixture with saturated NH₄Cl solution and extract two times with ethyl acetate. Wash the combined organic phases with saturated sodium chloride solution and dry them over sodium sulfate. Evaporate the solvents under vacuum. This gives 5 g of a colorless oil, which is chromatographed on silica gel (heptane/ethyl acetate=9/1) to give 4-(1-ethyl-1-hydroxypropyl)-2-methylphenylboronic acid in the form of a highly viscous oil. (Yield=71%)

¹H NMR (CDCl₃; 400 MHz): 0.78 (t; 3H; J₂=7.4 Hz); 1.86 (broad unresolved peak; 4H); 2.86 (s; 3H); 7.31 (m; 3H); 8.22 (d; 1H; Jo=8.3 Hz)

Example 3

Synthesis of 3-[3-Propyl-4-(4,4,5,5-tetramethyl-[1,3,2]dioxaborolan-2-yl)phenyl]pentan-3-ol In a three-necked flask, introduce under nitrogen 2 g of 3-(4-bromo-3-propylphenyl)pentan-3-ol (7 mmol) and 20 cm³ of N,N-dimethylformamide. Add 2.06 g (21 mmol) of potassium acetate and 1.87 g (7.3 mmol) of bis(pinacol)diborane. Add 0.229 g (0.28 mmol) of dichloro[1.1'-ferrocenylbis (diphenylphosphane)]palladium(II) dichloromethane [Pd(dppf)Cl₂] and heat the reaction mixture at reflux for 2 h 30 min. Hydrolyse the mixture and extract it twice with ethyl acetate. Wash the combined organic phases with saturated sodium chloride solution and evaporate the solvents under vacuum. This gives 3.6 g, which is chromatographed on silica gel (heptane/ethyl acetate=8/2). This gives 1.55 g of 3-[3-propyl-4-(4,4,5,5-tetramethyl[1,3,2]dioxaborolan-2-yl)phenyl]pentan-3-ol in the form of a highly viscous oil. (Yield=76%)

$^1$H NMR (CDCl$_3$; 400 MHz): 0.76 (t; 6H; J$_2$=7.4 Hz); 0.95 (t; 3H; J$_1$=7.3 Hz); 1.36 (s; 12H); 1.60 (broad unresolved peak; 2H); 1.67 (s; 1H); 1.84 (broad unresolved peak; 4H); 2.88 (t; 2H; J$_2$=7.6 Hz); 7.18 (m; 2H); 7.75 (d; 1H; Jo=8.4 Hz)

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A disubstituted phenylboronic acid compound of the following structural formula (I):

in which:
R1 is a hydrogen atom or an alkyl radical having from 1 to 4 carbon atoms,
R2 and R3, which may be identical or different, are each an alkyl radical having from 1 to 4 carbon atoms, and
R4 is the —B(OH)$_2$ radical or the radical of formula:

2. The disubstituted phenylboronic acid compound as defined by claim 1, wherein formula (I), each alkyl radical having from 1 to 4 carbon atoms is a saturated or unsaturated, linear or cyclic, optionally branched such radical and can be interrupted by a heteroatom.

3. The disubstituted phenylboronic acid compound as defined by claim 2, wherein formula (I), each alkyl radical is selected from the group consisting of methyl, ethyl, propyl, isopropyl, cyclopropyl, butyl, isobutyl and tert-butyl radicals.

4. A process for the preparation of a disubstituted phenylboronic acid compound (I) as defined by claim 1 wherein formula (I) R4 is the B(OH)$_2$ radical, comprising:

a) bromination of methyl 4-bromo-3-methylbenzoate into the compound (1):

b) substituting the bromine atom introduced in step a) by an alkyl radical R5 having from 1 to 4 carbon atoms to obtain a compound (2):

c) converting the ester function of the intermediate (2) or of methyl 4-bromo-3-methylbenzoate into a tertiary alcohol function by reaction with an organomagnesium compound of formula R2-MgX wherein X is a halogen and R2 is a methyl, ethyl, propyl or butyl radical, to obtain a compound (3):

d) converting the intermediate (3) into said disubstituted phenylboronic acid compound (I) in the presence of a base and a trialkyl borate, with the proviso that the steps a) and b) are omitted in the event that R1 is a hydrogen atom.

5. A process for the preparation of a disubstituted phenylboronic acid compound as defined by claim 1 wherein formula (I) R4 is the radical, comprising:

a) bromination of methyl 4-bromo-3-methylbenzoate into the compound (1):

(1)

b) substituting the bromine atom introduced in step a) by an alkyl radical R5 having from 1 to 4 carbon atoms to obtain a compound (2):

(2)

c) converting the ester function of the intermediate (2) or of methyl 4-bromo-3-methylbenzoate into a tertiary alcohol function by reaction with an organomagnesium compound of formula R2-MgX wherein X is a halogen and R2 is a methyl, ethyl, propyl or butyl radical, to obtain a compound (3):

(3)

d) converting the intermediate (3) into an aryl boronate in the presence of a base and a boron tetraalkyl and then into said disubstituted phenylboronic acid compound (I), with the proviso that the steps a) and b) are omitted in the event that R1 is a hydrogen atom.

6. The process as defined by claims 4 or 5, wherein step a) is carried out in the presence of at least one brominating agent selected from the group consisting of bromine, N-bromosuccinimide, sodium bromate and 1,3-dibromo-5,5-dimethylhydantoin and in a chlorinated or ether solvent.

7. The process as defined by claim 6, wherein step a) is carried out in the presence of N-bromosuccinimide in dichloromethane.

8. The process as defined by claims 4 or 5, wherein step a) is carried out in the presence of a free-radical initiator.

9. The process as defined by claims 4 or 5, wherein step b) is carried out in the presence of an organometallic reagent R'1-M in which M is magnesium, copper or zinc.

10. The process as defined by claim 9, wherein step b) is carried out in the presence of copper iodide and an organomagnesium compound R'1-MgX in which X is a bromine, chlorine or iodine atom.

11. The process as defined by claims 4 or 5, wherein step b) is carried out in an ethereal solvent.

12. The process as defined by claims 4 or 5, wherein step b) is carried out at a temperature of from −40° C. to −20° C.

13. The process as defined by claims 4 or 5, wherein step c) is carried out in an ethereal solvent at a temperature of from −10° C. to +10° C.

14. The process as defined by claim 4, wherein step d) is carried out in the presence of an ethereal solvent, a strong base and a trialkyl borate.

15. The process as defined by claim 14, wherein step d) is carried out in the presence of tetrahydrofuran, butyllithium and triisopropyl borate, at a temperature of from −78° C. to −40° C.

16. The process as defined by claim 5, wherein step d) is carried out in the presence of a DMF, tetrahydrofuran, DMSO or dioxane solvent, a dichloro [1,1'-ferrocenylbis(diphenylphosphane)]palladium(II) dichloromethane or Pd(dppf)Cl$_2$ catalyst, a potassium acetate or triethylamine base, and pinacolborane or pinacoldiborane.

\* \* \* \* \*